(12) United States Patent
Wendlandt

(10) Patent No.: US 7,988,702 B2
(45) Date of Patent: *Aug. 2, 2011

(54) SURGICAL CLIP WITH A SELF-RELEASING FLUID RESERVOIR

(75) Inventor: Jeffrey M. Wendlandt, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 869 days.

This patent is subject to a terminal disclaimer.

(21) Appl. No.: 11/066,324

(22) Filed: Feb. 25, 2005

(65) Prior Publication Data

US 2005/0228444 A1   Oct. 13, 2005

Related U.S. Application Data

(63) Continuation of application No. 10/072,697, filed on Feb. 7, 2002, now Pat. No. 6,869,436.

(51) Int. Cl.
*A61B 17/08* (2006.01)
(52) U.S. Cl. .................. 606/151; 606/213; 606/215
(58) Field of Classification Search .............. 606/151, 606/152, 153, 154, 155, 156, 157, 158, 75, 606/76, 77, 188, 213, 214, 215, 216, 217, 606/219, 220, 300, 322, 323, 329, 328; 424/422, 424/423, 424; 604/890.1, 891.1, 892.1
See application file for complete search history.

(56) References Cited

U.S. PATENT DOCUMENTS

| | | | |
|---|---|---|---|
| 1,918,889 A | 7/1933 | Bacon | |
| 2,367,657 A | 1/1945 | Boersma | |
| 3,069,962 A * | 12/1962 | Rapata | 411/510 |
| 3,254,650 A | 6/1966 | Collito | |
| 3,623,192 A | 11/1971 | Papazian | |
| 3,825,010 A | 7/1974 | McDonald | |
| 3,828,772 A | 8/1974 | Thiele | |
| 3,831,584 A | 8/1974 | Bucalo | |
| 3,918,455 A | 11/1975 | Coplan | |
| 4,532,926 A | 8/1985 | O'Holla | |
| 4,548,202 A | 10/1985 | Duncan | |
| 4,741,337 A * | 5/1988 | Smith et al. | 606/220 |

(Continued)

FOREIGN PATENT DOCUMENTS

| | | |
|---|---|---|
| EP | 0 531 742 A1 | 3/1993 |
| WO | WO 01/85034 A1 | 11/2001 |
| WO | WO 02/28298 A1 | 4/2002 |

OTHER PUBLICATIONS

Drugs.com "Iodine (Topical)", pp. 1-4; printed Sep. 20, 2004 to show that Iodine has antimicrobial effects (see p. 2).

(Continued)

*Primary Examiner* — Darwin P Erezo
*Assistant Examiner* — Jing Rui Ou
(74) *Attorney, Agent, or Firm* — Finnegan, Henderson, Farabow, Garrett & Dunner LLP

(57) ABSTRACT

The present invention generally relates to surgical clips. A surgical clip comprises a first piece comprising a first base and a first projection extending from the first base, a second piece comprising a second base, a second projection extending from the second base wherein the second projection further comprises a top surface, at least one side surface and a bottom surface, the surfaces defining a reservoir therein, and the first and the second piece are detachably connectable. In a preferred embodiment, the reservoir is self-releasing to deliver therapeutic materials when the first piece and second piece are connected.

11 Claims, 1 Drawing Sheet

U.S. PATENT DOCUMENTS

| | | | |
|---|---|---|---|
| 4,754,758 A | | 7/1988 | Li |
| 4,871,542 A | | 10/1989 | Vilhardt |
| 4,889,119 A | * | 12/1989 | Jamiolkowski et al. ...... 606/220 |
| 4,890,613 A | * | 1/1990 | Golden et al. ............... 606/220 |
| 4,935,028 A | | 6/1990 | Drews |
| 4,961,931 A | | 10/1990 | Wong |
| 4,976,715 A | | 12/1990 | Bays et al. |
| 4,994,073 A | | 2/1991 | Green |
| 5,013,316 A | | 5/1991 | Goble et al. |
| 5,016,369 A | | 5/1991 | Parry |
| 5,053,047 A | | 10/1991 | Yoon |
| 5,189,986 A | | 3/1993 | Burkoth |
| 5,226,908 A | | 7/1993 | Yoon |
| 5,282,829 A | | 2/1994 | Hermes |
| 5,293,881 A | * | 3/1994 | Green et al. ................. 128/898 |
| 5,383,897 A | | 1/1995 | Wholey |
| 5,403,312 A | | 4/1995 | Yates et al. |
| 5,423,858 A | | 6/1995 | Bolanos et al. |
| 5,461,805 A | * | 10/1995 | Johnson .......................... 40/301 |
| 5,474,572 A | | 12/1995 | Hayhurst |
| 5,486,195 A | | 1/1996 | Myers et al. |
| 5,516,522 A | * | 5/1996 | Peyman et al. ............... 424/426 |
| 5,549,122 A | | 8/1996 | Detweilwer |
| 5,562,694 A | | 10/1996 | Sauer et al. |
| 5,569,272 A | | 10/1996 | Reed et al. |
| 5,571,216 A | | 11/1996 | Anderson |
| 5,582,616 A | | 12/1996 | Bolduc et al. |
| 5,591,206 A | | 1/1997 | Moufarrege |
| 5,630,831 A | | 5/1997 | Lahr |
| 5,634,936 A | | 6/1997 | Linden et al. |
| 5,649,937 A | | 7/1997 | Bito et al. |
| 5,662,683 A | | 9/1997 | Kay |
| 5,667,513 A | | 9/1997 | Torrie et al. |
| 5,792,115 A | | 8/1998 | Horn |
| 5,800,544 A | * | 9/1998 | Demopulos et al. ....... 623/13.13 |
| 5,817,054 A | | 10/1998 | Grimm |
| 5,944,738 A | | 8/1999 | Amplatz et al. |
| 5,993,476 A | | 11/1999 | Groiso |
| 6,059,766 A | | 5/2000 | Greff |
| 6,077,281 A | * | 6/2000 | Das ............................... 606/151 |
| 6,086,600 A | | 7/2000 | Kortenbach |
| 6,095,915 A | | 8/2000 | Geissler et al. |
| 6,099,552 A | | 8/2000 | Adams |
| 6,113,609 A | | 9/2000 | Adams |
| 6,120,526 A | | 9/2000 | Daley |
| 6,126,677 A | | 10/2000 | Ganaja et al. |
| 6,482,197 B2 | | 11/2002 | Finch et al. |
| 6,569,173 B1 | | 5/2003 | Blatter et al. |
| 6,596,013 B2 | | 7/2003 | Yang et al. |
| 6,605,090 B1 | * | 8/2003 | Trieu et al. ...................... 606/69 |
| 2002/0035370 A1 | | 3/2002 | Kortenbach |
| 2002/0156344 A1 | | 10/2002 | Pasricha et al. |
| 2003/0040761 A1 | | 2/2003 | Pugsley et al. |
| 2003/0149439 A1 | | 8/2003 | Wendlandt |
| 2003/0220660 A1 | | 11/2003 | Kortenbach et al. |
| 2004/0208909 A1 | | 10/2004 | Brubaker et al. |

OTHER PUBLICATIONS

Steadman's Medical Dictionary 27$^{th}$ Edition "asepsis" printed Sep. 20, 2004 to show that asepsis is sterility (or the absence of germs).
Trauma Research Projects, pp. 1-3. Included to show that hypertonic saline has anti-inflammatory effects on the body.

* cited by examiner

SURGICAL CLIP WITH A SELF-RELEASING FLUID RESERVOIR

This is a continuation of application Ser. No. 10/072,697, filed Feb. 7, 2002 now U.S. Pat. No. 6,869,436, which is incorporated herein by reference.

FIELD OF THE INVENTION

The present invention generally relates to surgical clips used to secure tissue together. More specifically, the present invention relates to surgical clips with a self-releasing reservoir to deliver therapeutic materials.

BACKGROUND OF THE INVENTION

The present invention relates to clips for surgical procedures. Surgical clips are routinely used to secure tissue together during or after many differing surgical procedures. In most instances, a surgical procedure will result in at least one incision that requires closing. In addition, damaged or broken blood vessels, ligaments, bone, tendons, skin and other tissues may also require a means for securing. Surgical clips, preferably, are used to perform the function of securing these and other tissues together.

Surgical clips are known in the prior art and are available in a wide variety of shapes and styles. Generally, the clips comprise one or two pieces. In the case of one-piece clips, the clip will typically fold and lock onto itself while holding tissue in the fold. Similarly, two-piece clips typically secure tissue by holding tissue between the clips when they are brought together. In addition to clips, other devices are known in the prior art that are used to secure tissue together. These devices include clamps, staples, sutures, etc.

Surgical clips generally secure tissue together in the hope that the tissue will then fuse together over a period. In order to facilitate this process, it is often necessary to administer a therapeutic agent to assist with the repair of the tissue. The therapeutic agent may include sclerosing agents or pharmacological drugs.

Sclerosing agents are believed to irritate tissue, which in turn encourages the tissue to heal. Using a surgical clip in conjunction with a sclerosing agent may facilitate healing. Presently, a therapeutic agent needs to be delivered independently of using surgical clips. For example, a physician can administer a therapeutic agent to a desired area before or after securing tissue together. Surgical clips that possess the ability to deliver a sclerosing agent to tissue in need of being secured together could improve these processes and offer enhanced convenience.

Additionally, it may be necessary to administer a pharmacological agent. In general, it may be desired to administer a drug that can promote hemostasis. These drugs may promote healing by increasing adhesion and activation of platelets, increasing fibrin formation, or increasing vascular contraction. Typically, a physician may administer a pharmacological agent to an area of interest before or after securing tissue together. By combining the ability to secure tissue and to deliver a pharmacological drug, the process of clipping tissue may be more convenient and the over-all treatment improved.

Further, many modern surgical techniques are designed to be as non-invasive as possible. For these surgical techniques, specialized equipment is used that minimizes the size of an incision. For example, specialized clips and clipping techniques are required. Specialized clips are known that enable the joining of tissue when accessibility is limited. For example, clips are known that can be inserted into an incision in order to join ends of tissue below an incision. However, the delivery of a therapeutic agent would still need to take place independently of using the clip. The delivery of a therapeutic agent would, therefore, require additional specialized equipment. A need, therefore, exists for surgical clips sized for specialized medical procedures that can deliver therapeutic agents such as a sclerosing agent or pharmacological drug in conjunction with medical procedures.

SUMMARY OF THE INVENTION

The present invention generally relates to surgical clips used to secure tissue together. In a preferred embodiment, a surgical clip comprises a first piece, a second piece, and a self-releasing reservoir disposed within at least one of the pieces that is activated during clipping of tissue and allows for the delivery of a therapeutic agent.

According to a preferred embodiment, the first piece comprises a first base and a first projection extending from the first base. Preferably, the first base is generally circular. In an exemplary embodiment, the first projection extends substantially perpendicular relative to the first base and is generally cylindrical in shape. In preferred embodiments, the first projection includes a proximal portion and a distal portion. The proximal portion is preferably generally cylindrical having an outside diameter smaller than that of the first base. The distal portion of the first projection is preferably conical in shape and includes a distal end defined by the tip of the conical shape and a proximal end defined by the base of the conical shape. The conical shaped distal portion is a preferred means for penetrating the tissue to be clipped and a preferred means for interacting with the second piece of the surgical clip described below. The base of the conical shaped distal portion is preferably generally circular and of a diameter greater than the proximal portion of the first projection. As such, the base of greater diameter provides an edge or radially projecting edge surface relative to the proximal portion of the first projection, providing a surface which releasably secures the first piece of the clip to the second piece as described in detail below. Preferably, the first piece is constructed of bioabsorbable materials.

In a preferred embodiment, the second piece comprises a second base and a second projection extending from the second base. Preferably, the second base is generally circular and of greater diameter than the second projection. According to a preferred embodiment, the second projection extends substantially perpendicular relative to the second base. In an exemplary embodiment, the second projection is generally cylindrical in shape. Preferably, the second piece is constructed of bioabsorbable materials.

In a preferred embodiment, the second projection further comprises a top surface, at least one side surface and a bottom surface. These surfaces define a reservoir. Preferably, the reservoir contains a selected amount of a therapeutic agent, for example a sclerosing agent or pharmacological drug.

According to a preferred embodiment, the first piece and the second piece are detachably connectable. Preferably, the first projection and the second projection are shaped suitably to mate when brought together. In a preferred embodiment, the second projection comprises a means to slidably receive the first projection. In an alternative embodiment, the first projection receives the second projection.

In a preferred embodiment, detachably connecting the first piece and the second piece allows the release of a therapeutic agent from the reservoir. According to a preferred embodiment, the front surface overlies the hollow reservoir. In an exemplary embodiment, the front surface comprises puncturable material so that connecting the first piece and the second piece allows at least the distal portion of the first projection to pierce the front surface. Piercing the front surface preferably releases the therapeutic agent from the reservoir.

In a preferred embodiment, the second projection further comprises at least one aperture sized to allow the flow of a therapeutic agent out of the reservoir. According to a preferred embodiment, when the first piece and the second piece are detachably connected, a therapeutic agent can flow out from the reservoir through the apertures which are preferably located in the side wall between the top and bottom surfaces.

In a preferred embodiment, tissue in need of being secured can be secured together by placing the first piece and the second piece in the proximity of the tissue. Preferably, when the first piece and the second piece are detachably connected, they secure the tissue together. Detachably connecting the first piece and the second piece results in the flow of a therapeutic agent from the reservoir to an area of interest proximate a tissue in need of being secured. In an exemplary embodiment, when the first piece and the second piece are connected, a therapeutic agent is released from at least one aperture contained within the second projection.

According to multiple embodiments of the current invention, tissue in need of being secured together may include, but is not limited to, a blood vessel, a ligament, a bone, a tendon, and skin. In an exemplary embodiment, the surgical clips can be sized for specialized surgical techniques. Preferably, the clips can be small enough to enter an incision in order to join tissue below the incision. A person of ordinary skill in the art would be familiar with determining tissue appropriate for multiple embodiments of the current invention.

DETAILED DESCRIPTION OF THE PREFERRED EMBODIMENTS

Figure 1:
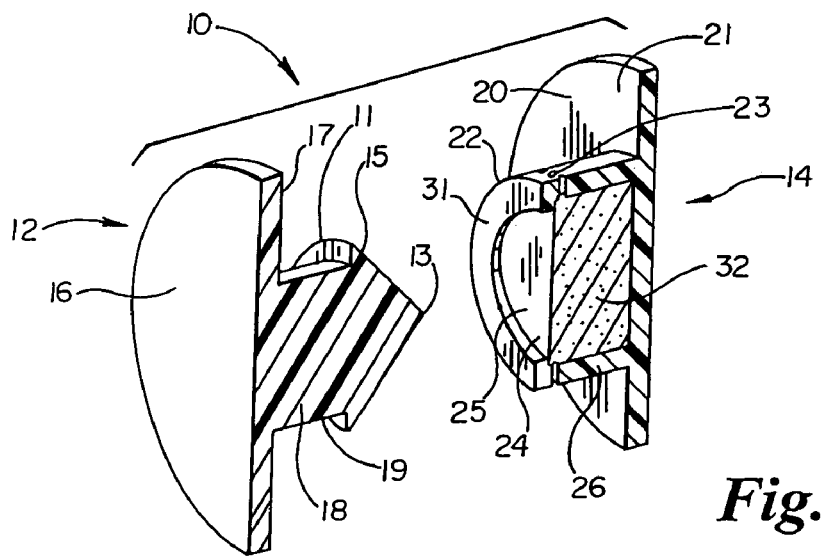
FIG. 1 is a perspective cross-sectional view depicting a surgical clip according to a preferred embodiment of the current invention.

Referring now to the drawings wherein like reference numerals indicate like elements throughout the several views, FIG. 1 depicts a surgical clip according to a preferred embodiment of the current invention. Preferably, the surgical clip can be used in conjunction with a medical procedure to secure tissue together. In an exemplary embodiment, the surgical clip can be used to secure tissue together and concurrently deliver a therapeutic agent.

In a preferred embodiment, surgical clip 10 comprises first piece 12 and second piece 14. First piece 12 and second piece 14 are preferably constructed of bioabsorbable materials. Bioabsorbable materials can include, but are not limited to, poly(L-lactide) (PLLA), poly(D,L-lactide) (PLA), poly(glycolide) (PGA), poly(L-lactide-co-D.L. Lactide) (PLLA/PLA), poly(L-lactide-co-glycolide) (PLA/PGA), poly(glycolide-co-trimethylene carbonate) (PGA/PTMC), polydioxanone (PDS), polycaprolactone (PCL), polyhydroxybutyrate (PHBT), poly(phosphazenes), poly(D,L-lactide-co-caprolactone) (PLA/PCL), poly(glycolide-co-caprolactone) (PGA/PCL), poly(phosphase ester) and polyanhydrides. A person of ordinary skill in the art would be familiar with choosing an appropriate material for constructing first piece 12 and second piece 14 according to multiple embodiments of the current invention. The materials could be selected from any biocompatible material for selected permanent or temporary application.

Preferably, embodiments of the invention include surgical clips sized for differing surgical procedures. In one preferred embodiment, surgical clip 10 can be sized appropriately to enter an incision in order to join tissue below the incision. One of ordinary skill in the art would be familiar with choosing an appropriate size of surgical clip 10 according to a selected use of the current invention.

First piece 12 further comprises first base 16 and first projection 18 extending from first base 16. First base 16 is preferably generally circular. According to a preferred embodiment, first projection 18 extends substantially perpendicular from first piece 12 relative to first base 16. Further, first base 16 is preferably of larger diameter than first projection 18 so that in use, first projection 18 is inserted through tissue which is to be secured, while first base 16 provides an enlarged planar surface 17 which contacts tissue proximate first projection 18 and holds it in place.

Second piece 14 further comprises a second base 20 and a second projection 22 extending from the second base 20. In an exemplary embodiment, second base 20 is generally circular. Preferably, second projection 22 is substantially cylindrical in shape. According to a preferred embodiment, second projection 22 extends substantially perpendicular from second piece 14 relative to second base 20. As with first piece 12, second base 20 is preferably of larger diameter than second projection 22 so that in use, second projection 22 is inserted through tissue to be secured, while second base 20 provides an enlarged planar surface 21 which contacts tissue proximate second projection 22 and holds it in place.

In a preferred embodiment of the current invention, second projection 22 further comprises top surface 24, at least one side surface 26 and bottom surface 30. Bottom surface 30 preferably comprises a portion of second base 20. In an exemplary embodiment, second base 20 is hollow. In a preferred embodiment, top surface 24, side surface 26 and bottom surface 30 define reservoir 32 which, as previously stated, is preferably cylindrical in shape.

First piece 12 and second piece 14 are designed so that in use the two pieces cooperate to form a unitary, preferably releasably secured surgical clip 10 having enlarged planar surfaces 17 and 21 opposing each other and holding secured tissue therebetween. As depicted in FIG. 1, structural features have been incorporated into first projection 18 and second projection 22 to provide means for securing the first piece 12 to the second piece 14. Second piece 14 includes second projection 22 which preferably is generally cylindrical in shape and having a hollow reservoir 32 therein. The top surface 24 of the second projection 22 preferably incorporates a rim portion 31 which includes an opening of diameter slightly smaller than the inside diameter of the cylindrical shape defined by the second projection 22. This rim member 31 cooperates with the first projection 18 of first piece 12 to secure the members together.

Figure 3:
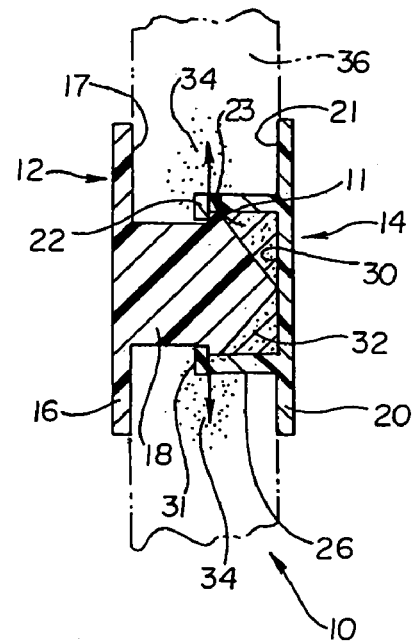
FIG. 3 is a cross-sectional view of the surgical clip of FIG. 2, wherein the first piece and the second piece are detachably connected and a therapeutic substance is released therefrom.

To cooperate with the above-described design of second piece 14, the first projection 18 preferably includes a proximal portion 19 and a distal portion 15. The proximal portion 19 is preferably generally cylindrical and has an outside diameter smaller than that of the base as described above. The distal portion 15 of the first projection 18 is preferably generally conical in shape and includes a distal end 13 defined by the tip of the conical shape at a proximal end 11 defined by the base of the conical shape. The conical shaped distal portion is a preferred means for penetrating the tissue to be clipped and a preferred means for interacting with the second piece 14 of the surgical clip. The base 11 of the conical shaped distal portion 15 is preferably generally circular and of a diameter greater than the proximal portion 19 of the first projection 18. As such, the base 11 of greater diameter provides an edge or radially projecting edge surface relative to the proximal portion 19 of the first projection 18. This surface secures the two pieces of the clip together when this portion passes through the rim portion 31 of the second piece 14. FIG. 3 depicts these pieces secured together as described.

Preferably, top surface 24 comprises a puncturable material portion 25 filling the opening through rim portion 31. According to a preferred embodiment, connecting first piece 12 and second piece 14, as described above results in the puncture of puncturable material portion 25 of top surface 24. One of ordinary skill in the art would be familiar with puncturable materials appropriate for selected embodiments of the current invention. Bioabsorbable polymeric films would be especially suitable for use.

In a preferred embodiment, second projection 22 further comprises at least one aperture 23 sized to allow the flow of a therapeutic agent 34 out of reservoir 32. According to a preferred embodiment, detachably connecting first piece 12 and second piece 14 results in the release of a therapeutic agent through aperture 23.

In alternative embodiments, first piece 12 and second piece 14 are detachably connectable utilizing other known designs wherein second piece 14 comprises a cross-sectional profile adapted to mate with first projection 18 of first piece 12. In each preferred embodiment, first piece 12 is adapted to pierce top surface 24 of second projection 22.

Reservoir 32, defined by second projection 22, preferably contains a predetermined amount of a therapeutic agent. The therapeutic agent may include, but is not limited to, a sclerosing agent or a pharmacological agent. For example, sclerosing agents may include; but are not limited to, sodium morrhuate, ethanolamine oleate, sotradecol, polidocanol, scleremo, hypertonic saline, sclerodex, and polyiodinated iodine.

Alternatively, for example, pharmacological agents may include, but are not limited to, vitamin K (phytomenadione), menadiol sodium diphosphate, warfarin, low-molecular-weight lieparins (LMWHs), heparin, protamine sulfate, dermatan sulfate, and any other drug affecting hemostasis. Numerous pharmacological agents have been set forth in the foregoing description. It will be understood, however, that this disclosure is, in many respects, only illustrative and that multiple other pharmacological agents could be used in place of the list above.

Figure 2:
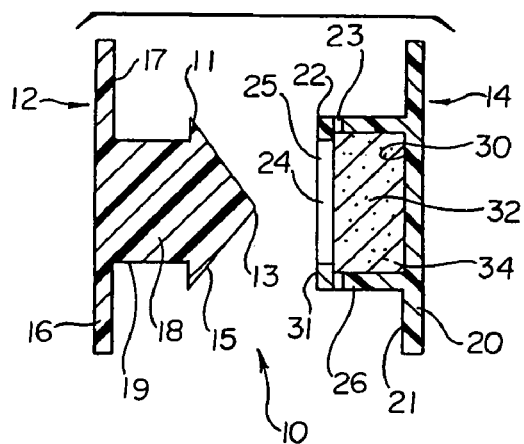
FIG. 2 is a cross-sectional view of the surgical clip of FIG. 1 depicting an arrangement appropriate for detachably connecting a first piece and a second piece.

FIG. 2 is a cross-sectional view of a surgical clip in an arrangement appropriate for detachably connecting the first piece and second piece. First piece 12 and second piece 14 of surgical clip 10 are detachably connectable. First piece 12 comprises first projection 18 extending from first base 16. Second piece 14 comprises second projection 22 extending from second base 20. Second piece 14 further comprises top surface 24, side surface 26, and bottom surface 30 that define reservoir 32. In a preferred embodiment of the current invention, reservoir 32 contains therapeutic agent 34.

Preferably, first projection 18 and second projection 22 are shaped suitably to mate when brought together. In a preferred embodiment, second projection 22 comprises a means to slidably receive first projection 18. In an alternative embodiment, first projection 18 slidably receives second projection 22.

In a preferred embodiment, detachably connecting first piece 12 and second piece 14 causes the release of therapeutic agent 34 from reservoir 32. According to a preferred embodiment, top surface 24 is hollow. In an exemplary embodiment, top surface 24 comprises puncturable material 25 over the opening in rim portion 31 so that connecting first piece 12 and second piece 14 allows first projection 18 to pierce top surface 24. Piercing top surface 24 preferably begins release of therapeutic agent 34 from reservoir 32 through apertures 23.

FIG. 3 depicts the surgical clip of FIG. 2, wherein the first piece and second piece are detachably connected.

Second piece 14 is depicted with a cross-sectional profile that is mated with first projection 18 of first piece 12. First piece 12 has pierced the top surface 24 of second projection 22. Planar surfaces 17 and 21 oppose each other to secure tissue 36 together. First projection 18 and second projection 22 pass through the tissue 36. As shown, therapeutic agent 34 has been released from reservoir 32 of second projection 22 through the at least one aperture 23.

According to multiple embodiments of the current invention, tissue 36 in need of being secured together may include, but is not limited to, a blood vessel, a ligament, a bone, a tendon, and skin. A person of ordinary skill in the art would be familiar with determining tissue appropriate for multiple embodiments of the current invention.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A surgical fastener for fastening tissue segments having tissue surfaces, the fastener comprising:
   a first fastener member; and
   a second fastener member configured to receive and retain the first fastener member and implantable within the body such that the tissue segments to be fastened are retained between the first and second fastener members and bodily fluid flow through the fastener members is substantially prevented, wherein the second fastener member includes a projection that extends from a base of the second fastener member towards the first fastener member when the second fastener member retains the first fastener member, the projection including a substantially cylindrical side wall that extends from the base towards the first fastener member when the second fastener member retains the first fastener member and an end face opposite the base, wherein the base, the side wall, and the end face of the projection define a reservoir containing a therapeutic agent therein, and wherein the side wall includes a plurality of apertures that extend transversely through the side wall and are positioned closer to the end face of the projection than to the base, at least one of the plurality of apertures having a perimeter that is completely circumscribed by the side wall, wherein at least two of the plurality of apertures are positioned opposite each other within the side wall with the reservoir therebetween, wherein the base of the second fastener member is substantially circular and the projection is substantially centrally positioned thereon.

2. The fastener according to claim 1, wherein the first fastener member comprises a base and a piercing element connected to the base for piercing the tissue segments to be fastened.

3. The fastener according to claim 2, wherein the end face of the second fastener member is configured to be pierced by the piercing element of the first fastener member.

4. The fastener according to claim 1, wherein the plurality of apertures are configured to deliver the therapeutic agent from the reservoir of the second fastener member to the tissue segments.

5. The fastener according to claim 1, wherein the side wall extends past the end face in a direction away from the base of the second fastener member to form a rim portion of the side wall.

6. The fastener according to claim 1, wherein the end face includes a puncturable material, wherein engagement between the first and second fastener members causes the first fastener member to pierce the puncturable material, thereby allowing delivery of the agent from the reservoir to the tissue segments.

7. The fastener according to claim 1, wherein each of the plurality of apertures is positioned below a top surface of the projection, the apertures defining passageways into the projection.

8. A method of fastening surfaces of tissue segments, comprising:
piercing the tissue segments to be fastened with a tissue fastener, the tissue fastener including a first fastener member and a second fastener member, the second fastener member being configured to receive and retain the first fastener member and implantable within the body such that the tissue segments to be fastened are retained between the first and second fastener members and bodily fluid flow through the fastener members is substantially prevented, wherein the second fastener member includes a projection that extends from a base of the second fastener member towards the first fastener member when the second fastener member retains the first fastener member, the projection including a substantially cylindrical side wall that extends from the base towards the first fastener member when the second fastener member retains the first fastener member and an end face opposite the base, wherein the base, the side wall, and the end face of the projection define a reservoir containing a therapeutic agent therein, and wherein the side wall includes a plurality of apertures that extend transversely through the side wall and are positioned closer to the end face of the projection than to the base, at least one of the plurality of apertures having a perimeter that is completely circumscribed by the side wall, wherein at least two of the plurality of apertures are positioned opposite each other within the side wall with the reservoir therebetween, wherein the base of the second fastener member is substantially circular and the projection is substantially centrally positioned thereon;
retaining the tissue segments to be fastened between the first fastener member and the second fastener member of the tissue fastener; and
delivering the therapeutic agent to the interface between the surfaces of the tissue segments to be joined,
wherein the tissue segments are fastened so as to close a space between the tissue segments and substantially prevent bodily fluid flow through the parts of the tissue fastener.

9. The method of claim 8, wherein the therapeutic agent comprises at least one of a sclerosing agent and a pharmacological agent.

10. The method of claim 8, wherein piercing the tissue segments includes the end face of the second fastener member with the first fastener member.

11. The method of claim 10, wherein delivering the therapeutic agent comprises delivering the therapeutic agent from the projection through at least one of the plurality of apertures upon piercing of the end face.

* * * * *